US012806337B2

(12) United States Patent
Takeda

(10) Patent No.: US 12,806,337 B2
(45) Date of Patent: Nov. 24, 2026

(54) MEDICAL NEEDLE

(71) Applicant: TERUMO KABUSHIKI KAISHA, Tokyo (JP)

(72) Inventor: Norihiko Takeda, Ashigarakami-gun Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 343 days.

(21) Appl. No.: 18/733,715

(22) Filed: Jun. 4, 2024

(65) Prior Publication Data

US 2024/0324920 A1 Oct. 3, 2024

Related U.S. Application Data

(63) Continuation of application No. PCT/JP2022/045600, filed on Dec. 12, 2022.

(30) Foreign Application Priority Data

Dec. 27, 2021 (JP) ................................ 2021-211836

(51) Int. Cl.
*A61M 5/158* (2006.01)
*A61B 5/15* (2006.01)

(52) U.S. Cl.
CPC ....... *A61M 5/158* (2013.01); *A61B 5/150374* (2013.01); *A61B 5/150389* (2013.01);
(Continued)

(58) Field of Classification Search
CPC ........ A61B 5/150374; A61B 5/150381; A61B 5/150389; A61B 5/150412; A61B 5/150503; A61B 5/150519; A61B 5/150534; A61B 5/150541; A61B 5/150549; A61B 5/150564; A61B 5/150633; A61B 5/150694; A61B 5/150717; A61M 2205/02; A61M 5/158; A61M 5/162; A61M 5/1626
See application file for complete search history.

(56) References Cited

U.S. PATENT DOCUMENTS 4,655,764 A 4/1987 Sato

FOREIGN PATENT DOCUMENTS

| | | |
|---|---|---|
| CN | 111499988 | 8/2020 |
| EP | 4011419 | 6/2022 |

(Continued)

OTHER PUBLICATIONS

English Translation of the International Search Report and Written Opinion for International (PCT) Patent Application No. PCT/JP2022/045600, dated Feb. 21, 2023, 5 pages.

(Continued)

*Primary Examiner* — Shefali D Patel
(74) *Attorney, Agent, or Firm* — Sheridan Ross PC

(57) ABSTRACT

A medical needle includes a needle body, a hub, and a protector. The hub includes a first resin composition. The protector has a needle sheath that covers a part of the needle body. The needle sheath includes a second resin composition. The first resin composition and the second resin composition each contain polyvinyl chloride and a trimellitate. In the first resin composition, the trimellitate accounts for 10 to 20 phr. In the second resin composition, the trimellitate accounts for 40 to 50 phr.

20 Claims, 15 Drawing Sheets

(52) U.S. Cl.
CPC .. *A61B 5/150412* (2013.01); *A61B 5/150503* (2013.01); *A61B 5/150519* (2013.01); *A61B 5/150534* (2013.01); *A61B 5/150633* (2013.01); *A61B 5/150549* (2013.01); *A61B 5/150717* (2013.01)

(56) References Cited

FOREIGN PATENT DOCUMENTS

| | | | |
|---|---|---|---|
| JP | S59-118165 | | 7/1984 |
| JP | S59118166 A | * | 7/1984 |
| WO | WO 2021/029393 | | 2/2021 |

OTHER PUBLICATIONS

Extended Search Report for European Patent Application No. 22915690.6, dated Feb. 27, 2025, 8 pages.
English Translation of Official Action for Vietnam Patent Application No. 1-2024-04622, dated Jun. 24, 2026, 2 pages.

* cited by examiner

IDEAL CRYSTAL

AMORPHOUSNESS

MEDICAL NEEDLE

CROSS-REFERENCE TO RELATED APPLICATIONS

The present disclosure is a continuation of and claims benefit to PCT/JP2022/045600 filed on Dec. 12, 2022, entitled "MEDICAL NEEDLE" which claims priority to Japanese Patent Application No. 2021-211836 filed on Dec. 27, 2021. The entire disclosure of the applications listed above are hereby incorporated herein by reference, in their entireties, for all that they teach and for all purposes.

BACKGROUND

The present disclosure relates to a medical needle including a needle body, a hub, and a protector.

A blood sampling needle is a type of medical needle. A blood sampling needle is incorporated into, for example, a blood sampling kit for collecting blood from a subject (hereinafter also referred to as a "donor"). In this case, the blood sampling needle is connected to a bag through a tube. The blood sampling needle includes a hollow needle body, a hub, and a protector. A proximal portion of the needle body in a longitudinal direction is inserted into the hub. A distal portion of the needle body in the longitudinal direction is exposed from the hub. The distal portion is inserted into a blood vessel of the donor.

The tube is connected to the hub. The proximal portion of the needle body is connected to the tube through the hub. Therefore, the blood collected from the distal portion of the needle body passes through the hollow needle body and flows into the tube. The blood that has passed through the tube flows into the bag.

As described in Japanese Patent No. JPH0117381B, before use, a protector of a blood sampling needle is joined to a hub. Therefore, a distal portion exposed from the hub is covered with the protector. In other words, the distal portion is protected by the protector. When collecting blood with the blood sampling needle, a user who collects the blood twists the protector relative to the hub. With this operation, the protector is separated from the hub. The user pulls the separated protector away from the hub. Accordingly, the distal portion of the needle body is exposed from the protector.

Materials of the hub and the protector are both a resin composition. In the resin composition, a plasticizer is added to a base resin. The plasticizer maintains flexibility of the base resin. An example of the base resin includes polyvinyl chloride (PVC). Japanese Patent No. JPH0117381B discloses a phthalate or trimellitate as a preferable plasticizer when PVC is used as a base resin.

BRIEF SUMMARY

Among phthalates, di-2 ethylhexyl phthalate (hereinafter referred to as "DEHP") has been widely used in the related art. On the other hand, recently, trimellitates have been frequently employed as plasticizers. However, according to intensive studies by the present inventors, the properties of a hub and a protector prepared using a trimellitate are different from the properties of a hub and a protector prepared using DEHP. In other words, it is difficult to obtain desired properties simply by replacing DEHP with a trimellitate as a plasticizer. This causes a difficulty in separating the protector from the hub. In addition, there is a concern that the needle body is misaligned with the hub.

It is with respect to the above issues and other problems that the embodiments presented herein were contemplated.

According to at least one embodiment of the present disclosure, a medical needle includes: a needle body; a hub that supports a proximal portion of the needle body in a longitudinal direction; and a protector that protects the needle body, wherein the protector has a needle sheath that covers a portion of the needle body exposed from the hub, the needle sheath is separably joined to the hub, the hub includes a first resin composition and the needle sheath includes a second resin composition, the first resin composition contains polyvinyl chloride and a trimellitate which accounts for 10 to 20 parts per hundred resin ("phr"), and the second resin composition contains polyvinyl chloride and a trimellitate which accounts for 40 to 50 phr.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages are described herein and will be apparent to those skilled in the art upon consideration of the following Detailed Description and in view of the figures.

BRIEF DESCRIPTION OF THE SEVERAL VIEWS OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

Figure 1:
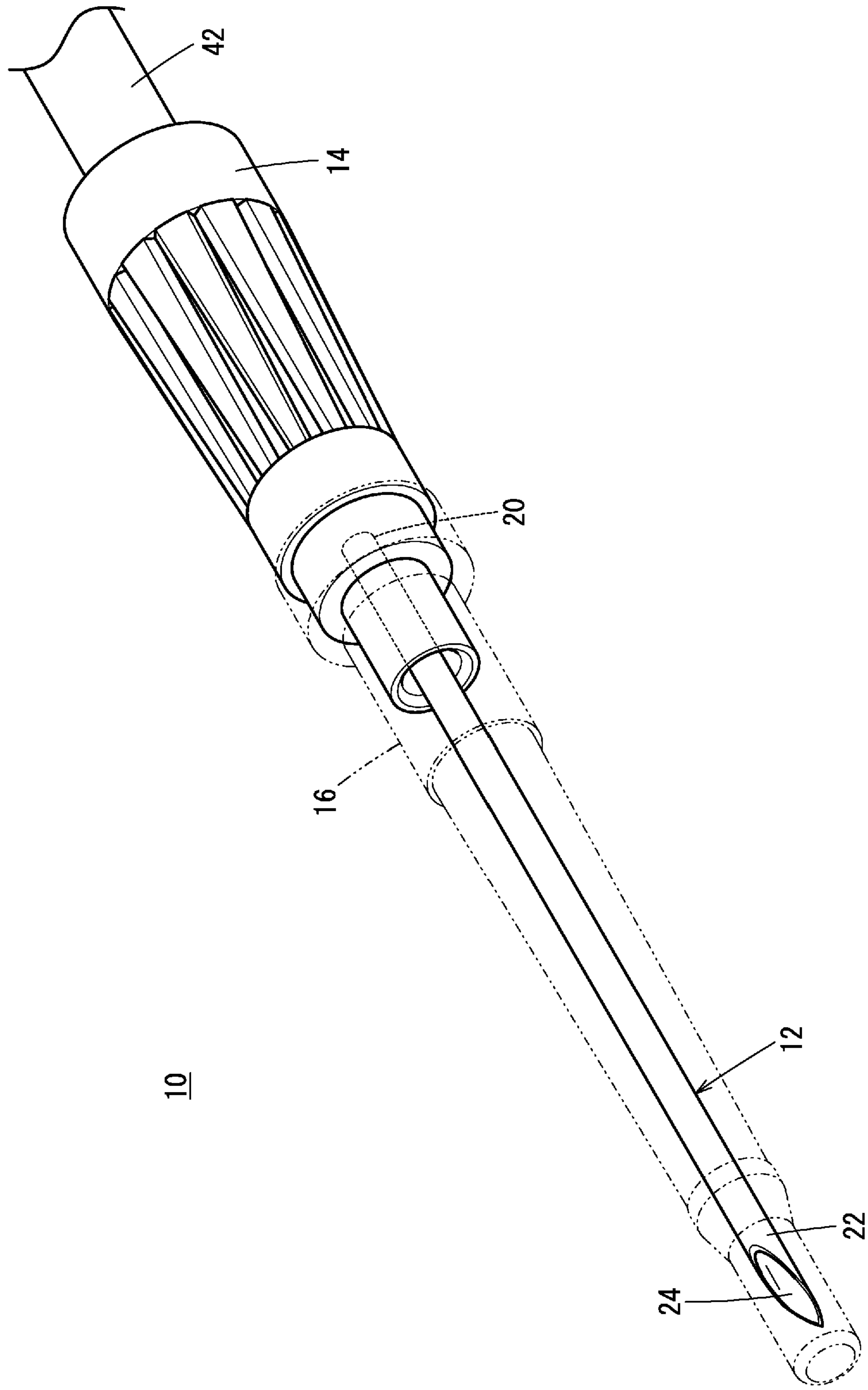
FIG. 1 is a perspective view of a blood sampling needle which is a type of medical needle in accordance with embodiments of the present disclosure.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

The ensuing description provides embodiments only, and is not intended to limit the scope, applicability, or configuration of the claims. Rather, the ensuing description will provide those skilled in the art with an enabling description for implementing the described embodiments. It being understood that various changes may be made in the function and arrangement of elements without departing from the spirit and scope of the appended claims.

It is with respect to the above issues and other problems that the embodiments presented herein were contemplated.

Hereinafter, a blood sampling needle will be illustrated as a medical needle according to embodiments of the present disclosure. However, the present disclosure is not particularly limited to the blood sampling needle shown and described herein.

Figure 2:
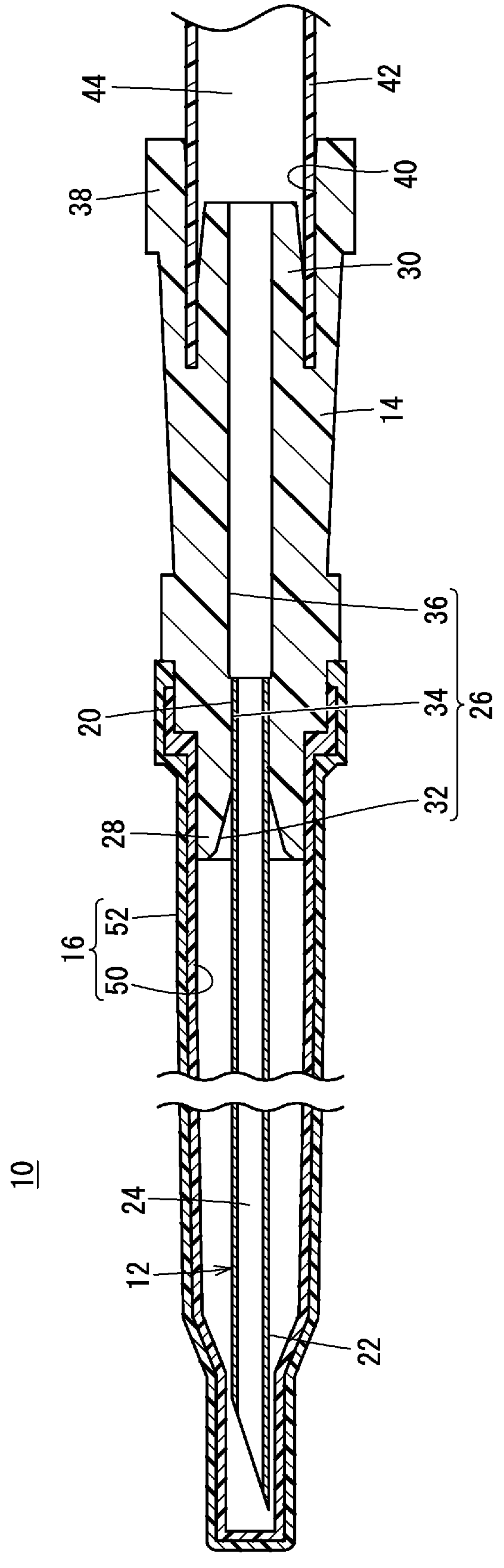
FIG. 2 is a longitudinal cross-sectional view of the blood sampling needle of FIG. 1 illustrating main parts of the blood sampling needle in accordance with embodiments of the present disclosure.

FIG. 1 is a perspective view of a blood sampling needle 10, or needle assembly. FIG. 2 is a longitudinal cross-sectional view illustrating main parts of the blood sampling needle 10. The blood sampling needle 10 includes a needle body 12, a needle hub 14 (e.g., hub), and a protector 16.

As illustrated in FIGS. 1 and 2, the needle body 12 is a circular tubular body having a small diameter and a long length (e.g., relative to the small diameter of the circular tubular body). The needle body 12 has a proximal portion 20, or one end in a longitudinal direction, and a distal portion 22, or the other end in the longitudinal direction. The needle body 12 is provided with a lumen 24. The lumen 24 is a blood channel, having a hollow interior extending from the proximal portion 20 to the distal portion 22. The lumen 24 makes the needle body 12 hollow.

The proximal portion 20 of the needle body 12 is inserted into the needle hub 14. Specifically, the needle hub 14 is provided with a through hole 26 extending along an axial direction of the needle hub 14. The through hole 26 in the needle hub 14 extends from a distal end face of a distal end 28 of the needle hub 14 that faces the needle body 12 to a protruding end surface of a protrusion 30 of the needle hub 14. The through hole 26 includes an introducing hole 32, a retaining hole 34, and a communicating hole 36. The introducing hole 32 opens at the distal end face of the distal end 28 in the needle hub 14. The retaining hole 34 is interposed between the introducing hole 32 and the communicating hole 36.

The introducing hole 32 is tapered, increasing in diameter from a proximal end 38 toward the distal end 28 of the needle hub 14. The proximal portion 20 of the needle body 12 is inserted from the introducing hole 32, and then, pushed into the retaining hole 34 of the needle hub 14. The proximal portion 20 of the needle body 12 is joined to the inner wall of the retaining hole 34 with an adhesive. For instance, the adhesive may be applied to one or more of the proximal portion 20 of the needle body 12 and/or the inner wall of the retaining hole 34 forming a bond at least disposed between the proximal portion 20 of the needle body 12 and the needle hub 14.

The proximal end 38 of the needle hub 14 is provided with an inserting groove 40. The cylindrical protrusion 30 is disposed on the bottom of the inserting groove 40. The protrusion 30 protrudes toward the proximal end 38 of the needle hub 14. However, the entire protrusion 30 is housed in the inserting groove 40. In other words, the protrusion 30 is not exposed from the inserting groove 40.

A distal end of the tube 42 is inserted into the inserting groove 40. The distal end of the tube 42 is fitted into the protrusion 30. A lumen 44 of the tube 42 is arranged in communication (e.g., fluid communication, etc.) with the lumen 24 of the needle body 12 through the communicating hole 36.

As illustrated in FIGS. 1 and 2, the protector 16 is a hollow member. The protector 16 has an inner layer 50 and an outer layer 52. In other words, the protector 16 has a double structure of the inner layer 50 and the outer layer 52. In some examples, this double structure of the inner layer 50 and the outer layer 52 may be referred to as a double-walled, or double-layered, structure. In any event, the inner layer 50 is a needle sheath that is arranged in a position that covers and shields the needle body 12. In the needle body 12, a portion covered by the inner layer 50 is exposed from the distal end 28 of the needle hub 14. In the needle body 12, the portion exposed (e.g., separated by a distance) from the distal end 28 of the needle hub 14 includes the distal portion 22. The outer layer 52 covers the inner layer 50. In other words, the inner layer 50 is housed in the outer layer 52. In this manner, the outer layer 52 serves as an outer sheath. In some examples, the outer layer 52 may be arranged in contact with and/or surrounding, or covering, one or more outermost portions or surfaces of the inner layer 50.

In the blood sampling needle 10, before the tube 42 is connected to the protrusion 30, a sealing film is applied to the opening of the inserting groove 40. In this state, the blood sampling needle 10 is sterilized with high-pressure steam. During the sterilization, at least the inner layer 50 or the outer layer 52 of the protector 16 is joined to the distal end 28 of the needle hub 14. Accordingly, a space between the protector 16 and the needle hub 14 is sealed in a state where the interior of the inner layer 50 (e.g., the housing space for the needle body 12) is kept sterile, or maintained in a sterile condition (e.g., sterile from a space surrounding an outside of the protector 16).

When using the blood sampling needle 10, a user holds the protector 16 with one hand and holds the needle hub 14 with the other hand. Next, the user twists the protector 16 or the needle hub 14. With this operation, the protector 16 and the needle hub 14 are separated from each other. Accordingly, the needle body 12 is exposed. Optionally, the protector 16 is attached to the needle hub 14 to cover the needle body 12. In this case, the protector 16 is detachable from the needle hub 14.

In this configuration, the needle hub 14 includes a first resin composition. The inner layer 50 of the protector 16 includes a second resin composition. In some examples, the first resin composition and the second resin composition are different from one another. The first resin composition and the second resin composition will now be described.

The first resin composition contains a base resin and a plasticizer. In this example, the base resin is polyvinyl chloride (PVC). The plasticizer is a trimellitate. Specific examples of the trimellitate include, but are in no way limited to, tributyl trimellitate and tris (2-ethylhexyl) trimellitate. Hereinafter, tris (2-ethylhexyl) trimellitate is also referred to as "TOTM". The following formula is the chemical structural formula of TOTM.

Chemical Formula 1

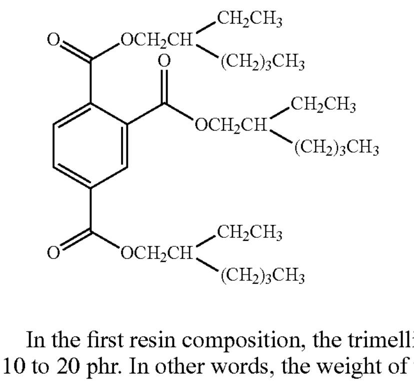

In the first resin composition, the trimellitate accounts for 10 to 20 phr. In other words, the weight of the trimellitate is 10 to 20 units when the weight of PVC as the base resin is 100 units. With less than 10 phr of the trimellitate, the hardness of the needle hub 14 increases (e.g., when compared to compositions including greater than 10 phr, etc.). The increased hardness makes it difficult to separate the protector 16 from the needle hub 14. In addition, it is not easy to attach the protector 16 to the needle hub 14 after separating the protector 16 from the needle hub 14. With over 20 phr of the trimellitate, the hardness of the needle hub 14 decreases (e.g., when compared to compositions including lower than 20 phr, etc.). The decreased hardness may cause concerns such as misalignment of the needle body 12 with the needle hub 14.

In other words, setting the proportion of the trimellitate within the range of 10 to 20 phr facilitates separation of the protector 16 from the needle hub 14 and attachment of the protector 16 to the needle hub 14. Furthermore, it is possible to maintain a state where the needle body 12 is firmly retained by the needle hub 14. In some examples, the trimellitate in the first resin composition may be selected to account for 13 to 18 phr.

The second resin composition contains a base resin and a plasticizer. In this embodiment, the base resin is PVC. The plasticizer is a trimellitate. Specific examples of the trimellitate include tributyl trimellitate and TOTM.

In the second resin composition, the trimellitate accounts for 40 to 50 phr. In other words, the weight of the trimellitate is 40 to 50 units when the weight of PVC as the base resin is 100 units. With less than 40 phr of the trimellitate, the hardness of the protector 16 increases (e.g., when compared to compositions including greater than 40 phr, etc.). The increased hardness requires large amounts of torque to be applied when separating the protector 16 from the needle hub 14. With over 50 phr of the trimellitate, the hardness of the protector 16 decreases (e.g., when compared to compositions including lower than 50 phr, etc.). The decreased hardness causes the protector 16 to squash slightly when the protector 16 is held. Furthermore, when the protector 16 is twisted relative to the needle hub 14, a joint between the protector 16 and the needle hub 14 extends. For these reasons, it is not easy to separate the protector 16 from the needle hub 14.

In other words, setting the proportion of the trimellitate within the range of 40 to 50 phr facilitates separation of the protector 16 from the needle hub 14. Further, when the proportion is set within the range of 40 to 50 phr, it is also easy to attach the separated protector 16 to the needle hub 14. In some examples, the trimellitate in the second resin composition may be selected to account for 45 to 47 phr.

In one embodiment, the materials of the inner layer 50 and the outer layer 52 are selected to have the same, or equal, properties as the second resin composition. In other words, the inner layer 50 and the outer layer 52 contain the same proportion of the trimellitate. In this case, the protector 16 is easily prepared. Alternatively, the second resin composition of the inner layer 50 and the second resin composition of the outer layer 52 may have different proportions of the trimellitate.

Materials of the inner layer 50 and the outer layer 52 may be different materials. Even in this case, the inner layer 50 is formed using the second resin composition as a material. In some cases, specific examples of the material for the outer layer 52 may include polyethylene and polycarbonate.

The blood sampling needle 10 according to this embodiment is configured as described above. Next, benefits and effects of the blood sampling needle 10 of the present disclosure will be described.

Before use, the blood sampling needle 10 is sterilized with high-pressure steam. During the sterilization, at least the inner layer 50 or the outer layer 52 of the protector 16 is joined to the distal end 28 of the needle hub 14.

When using the blood sampling needle 10, a user connects the distal end of the tube 42 to the protrusion 30 of the needle hub 14. Note that a proximal end of the tube 42 is connected to a bag (not illustrated) at this point in time. After that, the user holds the protector 16 and the needle hub 14. Next, the user twists the protector 16 relative to the needle hub 14 (e.g., rotating about an axis extending along the longitudinal direction of the needle body 12). With this operation, the joint between the protector 16 and the needle hub 14 is broken. In other words, the protector 16 is separated from the needle hub 14.

Herein, the material of the needle hub 14 may correspond to the first resin composition described above. The material of the protector 16 may correspond to the second resin composition described above. When joining the needle hub 14 including the first resin composition and the protector 16 including the second resin composition, it is possible to separate the protector 16 and the needle hub 14 with ease and with a smaller amount of rotary torque when compared to conventional designs.

Along with the separation of the protector 16 from the needle hub 14, the distal portion 22 of the needle body 12 is exposed from the protector 16. The user inserts the distal portion 22 of the needle body 12 into a blood vessel of a patient, subject, or donor. After being inserted, blood is collected from the blood vessel through the needle body 12. The blood flows into the bag through the lumen 24 of the needle body 12, the communicating hole 36 of the needle hub 14, and the lumen 44 of the tube 42. After a predetermined amount of blood is collected in the bag, the user draws the distal portion 22 of the needle body 12 from the blood vessel.

The material of the needle hub 14 may be set to correspond to the first resin composition. The needle hub 14 including the first resin composition provides an excellent retaining force with respect to the needle body 12 compared to conventional designs. Therefore, when the blood sampling needle 10 is drawn from the blood vessel, the needle body 12 moves in an integrated manner with the needle hub 14.

The protector 16 is put on the needle body 12 of the used blood sampling needle 10. In some examples, the protector 16 protects the needle body 12 before and/or after use. This prevents the needle body 12 from piercing any object (e.g., during handling, transit, etc.). The material of the needle hub 14 may be set to correspond to the first resin composition. The material of the protector 16 may be set to correspond to the second resin composition. When the protector 16 including the second resin composition is attached to the needle hub 14 including the first resin composition, the attachment is easy (e.g., requiring lower attachment forces than in conventional designs). With this composition, it is also easy to remove the protector 16 from the needle hub 14 after the attachment.

Note that the present disclosure is not limited to the examples and embodiments described herein, and various configurations may be adopted without departing from the gist of the present disclosure.

For example, the medical needle is not particularly limited to the blood sampling needle 10. Other specific examples of the medical needle may include an injection needle and a puncture needle.

EXAMPLE 1

According to a first example, a needle hub 14 is prepared from a first resin composition containing 15 phr of TOTM added to PVC. A proximal portion 20 of a needle body 12 is supported by the needle hub 14. On the other hand, a plurality of kinds of protectors 16 may be individually prepared from a second resin composition containing 45 phr, 46 phr, or 47 phr of TOTM added to PVC. After that, each protector 16 is attached to the needle hub 14, followed by sterilization with a high-pressure steam sterilizer. A plurality of kinds of blood sampling needles 10 is obtained through these steps.

Next, each protector 16 is retained by a clamp of a torque gauge. An inspector may hold the needle hub 14 with one hand and hold the torque gauge with the other hand. After that, rotary torque is applied to each protector 16, thereby measuring the rotary torque when each protector 16 is separated from the needle hub 14. Fifty blood sampling needles 10 may be measured to calculate an average rotary torque for the samples.

For comparison, a conventional blood sampling needle according to the related art is prepared. This blood sampling needle may be referred to hereinafter as the Comparative Example. The material of a needle hub in the Comparative Example is a resin composition obtained by adding DEHP to PVC. The material of a protector in the Comparative Example is a resin composition obtained by adding DEHP to PVC. In a similar manner as described in conjunction with the example blood sampling needles above, fifty blood sampling needles in the Comparative Example may be measured to calculate an average rotary torque when the protector is separated from the needle hub.

Figure 3:
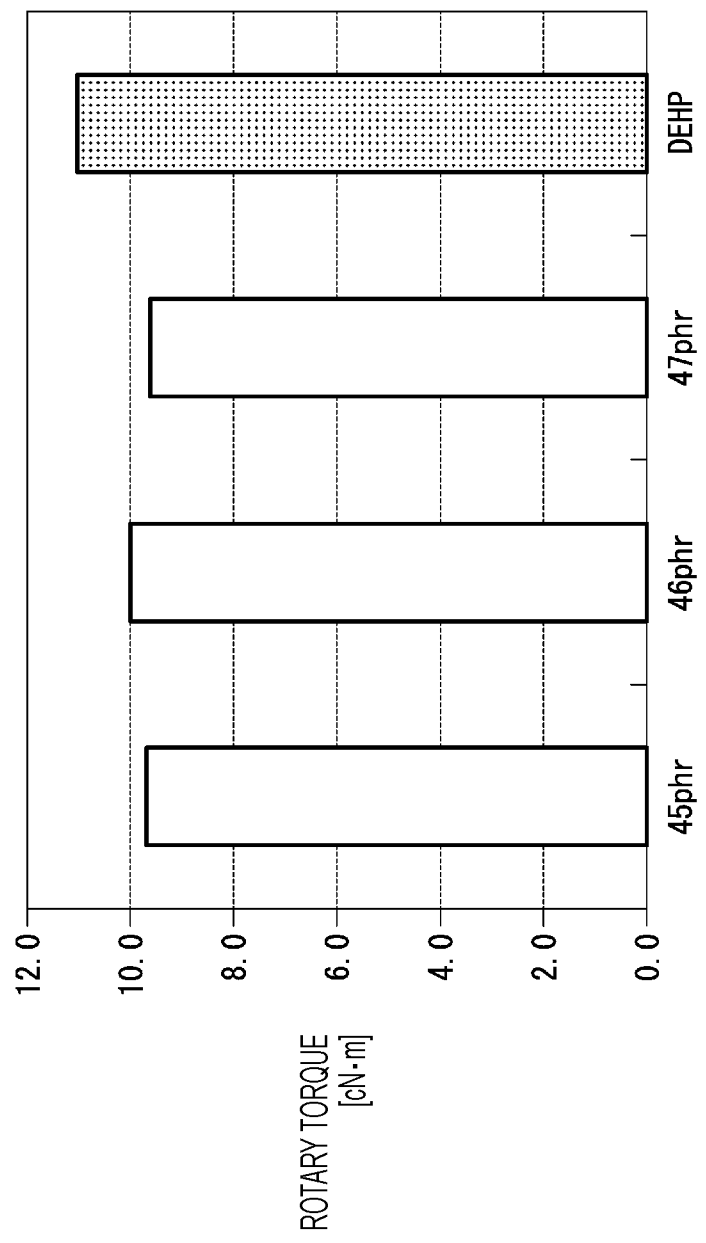
FIG. 3 is a graph illustrating average rotary torque when a protector is separated from a hub for various resin compositions in accordance with embodiments of the present disclosure.

The results are collectively illustrated in a graph in FIG. 3. In FIG. 3, the rotary torque is taken along the ordinate. The units of the rotary torque illustrated in FIG. 3 correspond to centinewton-meters, or cN·m. FIG. 3 illustrates that the average rotary torque of the blood sampling needle 10 according to the embodiments described in the first example is smaller than the average rotary torque required for the Comparative Example. Stated another way, the amount of rotary torque required to separate each protector 16 from the needle hub 14 according to embodiments of the present disclosure is lower than the torque required to separate the protector from the needle hub of the Comparative Example.

Although not particularly illustrated, when needle hubs 14 are prepared from a first resin composition obtained by adding 16 phr, 17 phr, or 18 phr of TOTM to PVC, substantially similar results to FIG. 3 are obtained. In other words, the blood sampling needle 10 according to this embodiment makes it easier to separate the protector 16 from the needle hub 14 than the blood sampling needle according to the related art or Comparative Example.

EXAMPLE 2

According to a second example, a plurality of kinds of needle hubs 14 are individually prepared from a first resin composition containing 15 phr, 16 phr, 17 phr, or 18 phr of TOTM added to PVC. A proximal portion 20 of a needle body 12 is supported by the needle hub 14. Next, each needle hub 14 is held by a stationary clamp, and the needle body 12 is held by a variable clamp. In this state, the variable clamp is moved in a direction away from the stationary clamp to impart tensile strength to the needle body 12. With this operation, the tensile strength when the needle body 12 is detached from each needle hub 14 is measured. One hundred test samples are measured to calculate average tensile strength. Similarly, one hundred test samples of the Comparative Example provided with no protector are measured to calculate average tensile strength.

Figure 4:
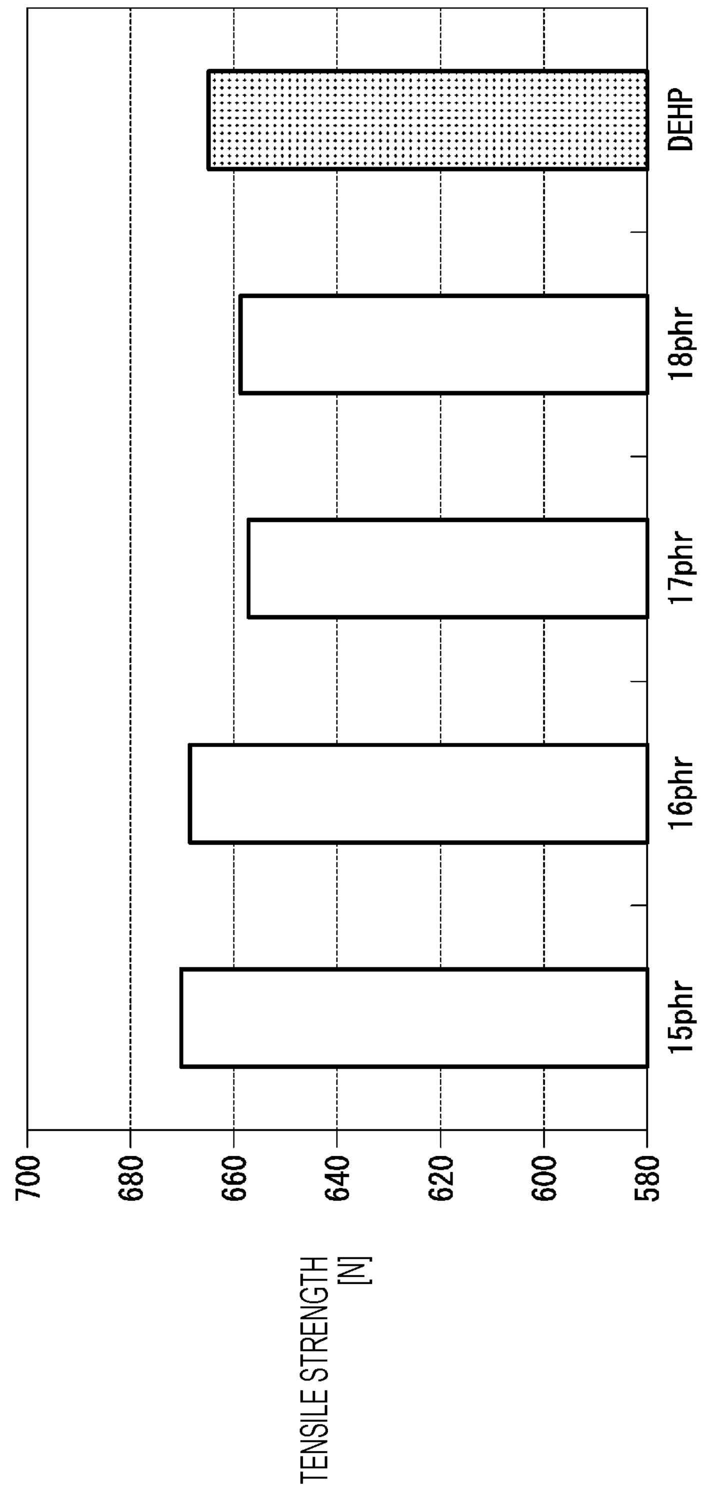
FIG. 4 is a graph illustrating average tensile strength when a needle body is drawn from the hub for various resin compositions in accordance with embodiments of the present disclosure.

The results are illustrated in FIG. 4. Note that the units of the ordinate shown in FIG. 4 is in newtons, N. FIG. 4 illustrates that the average tensile strength of the blood sampling needle 10 according to this embodiment is substantially equal to the average tensile strength in the Comparative Example. In other words, in this embodiment, the needle hub 14 of the present disclosure provides a sufficient retaining force with respect to the needle body 12 when compared to the Comparative Example. Therefore, it is unlikely that the needle body 12 is misaligned with the needle hub 14 in accordance with embodiments of the present disclosure.

EXAMPLE 3

According to a third example, a plurality of kinds of needle hubs 14 are individually prepared from a first resin composition containing 15 phr, 16 phr, 17 phr, or 18 phr of TOTM added to PVC. A proximal portion 20 of a needle body 12 is supported by the needle hub 14. On the other hand, a protector 16 is prepared from a second resin composition obtained by adding 45 phr of TOTM to PVC. After that, each protector 16 is attached to the needle hub 14, followed by sterilization with a high-pressure steam sterilizer. A plurality of kinds of blood sampling needles 10 is obtained through these steps.

After the protector 16 is separated from each needle hub 14, each needle hub 14 is held by a stationary clamp, and the protector 16 is held by a variable clamp. Next, the variable clamp is moved toward the stationary clamp, and the protector 16 is attached to each needle hub 14. In addition, the variable clamp is moved in a direction away from the stationary clamp, and the protector 16 attached to each needle hub 14 is drawn from each needle hub 14. An attachment/detachment force required for the attachment and the drawing is measured. One hundred blood sampling needles 10 are measured to calculate an average attachment/detachment force. Similarly, one hundred blood sampling needles in the Comparative Example are measured to calculate an average attachment/detachment force.

Figure 5:
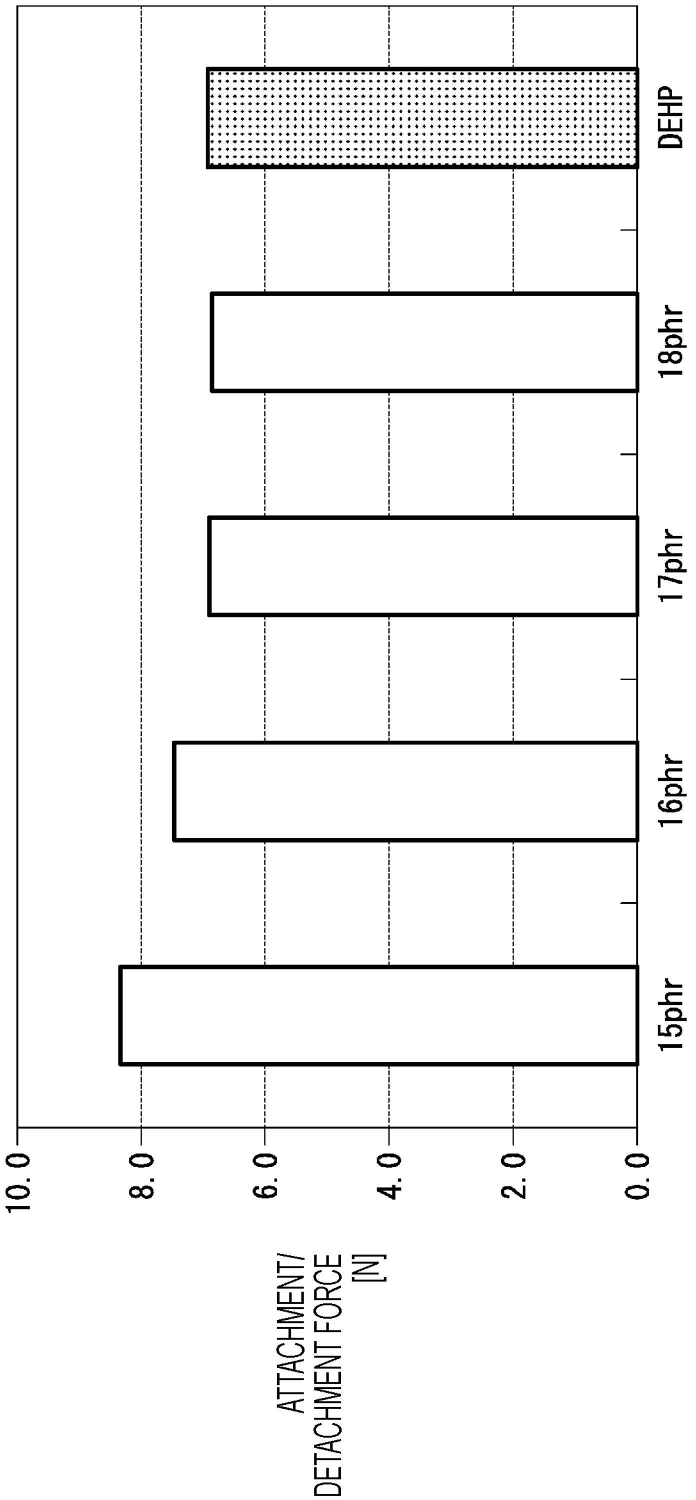
FIG. 5 is a graph illustrating an average attachment/detachment force when the protector is attached to and detached from the hub for various resin compositions in accordance with embodiments of the present disclosure.

The results are illustrated in FIG. 5. Note that the unit of the ordinate in FIG. 5 is newtons, N. FIG. 5 illustrates that the average attachment/detachment force of the blood sampling needle 10 according to this embodiment is substantially equal to the average attachment/detachment force in the Comparative Example. Although not particularly illustrated, when protectors 16 are prepared from a second resin composition obtained by adding 46 phr or 47 phr of TOTM to PVC, substantially similar results to FIG. 5 may be obtained.

In other words, in this embodiment, the present disclosure provides a blood sampling needle 10 where it is easy to attach the protector 16 to the needle hub 14 and to detach the protector 16 attached to the needle hub 14 from the needle hub 14.

EXAMPLE 4

According to a fourth example, a resin composition obtained by adding 45 phr of TOTM to PVC is molded into a cylindrical shape to obtain a molded article. An annular test sample is cut out from the molded article. This first test sample is referred to herein as Sample A. Another test sample having the same shape as that of Sample A is obtained from a resin composition obtained by adding 45 phr of DEHP to PVC. This second test sample is referred to herein as Sample B.

Figure 6:
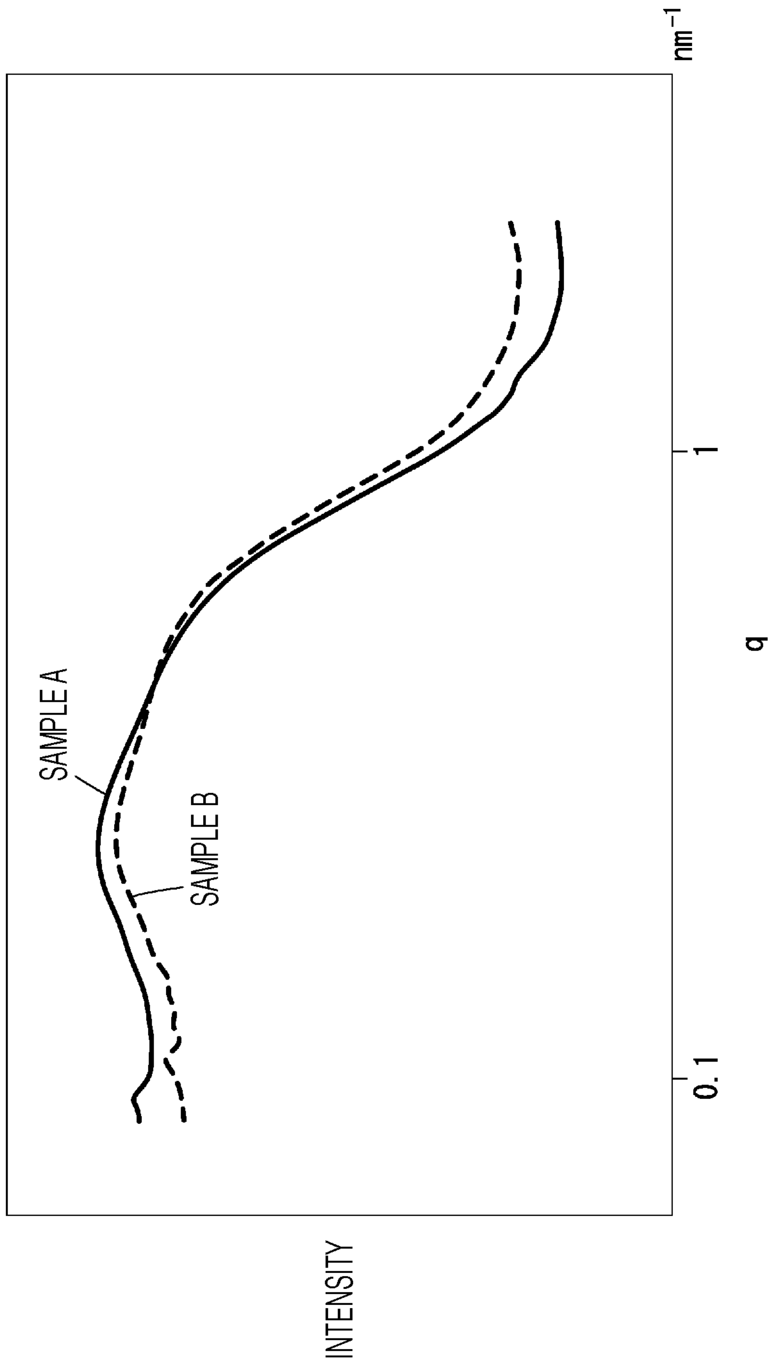
FIG. 6 illustrates small-angle X-ray scattering ("SAXS") scattering curves obtained by performing SAXS on a first sample labeled as Sample A and a second sample labeled as Sample B in accordance with embodiments of the present disclosure.
Figure 7:
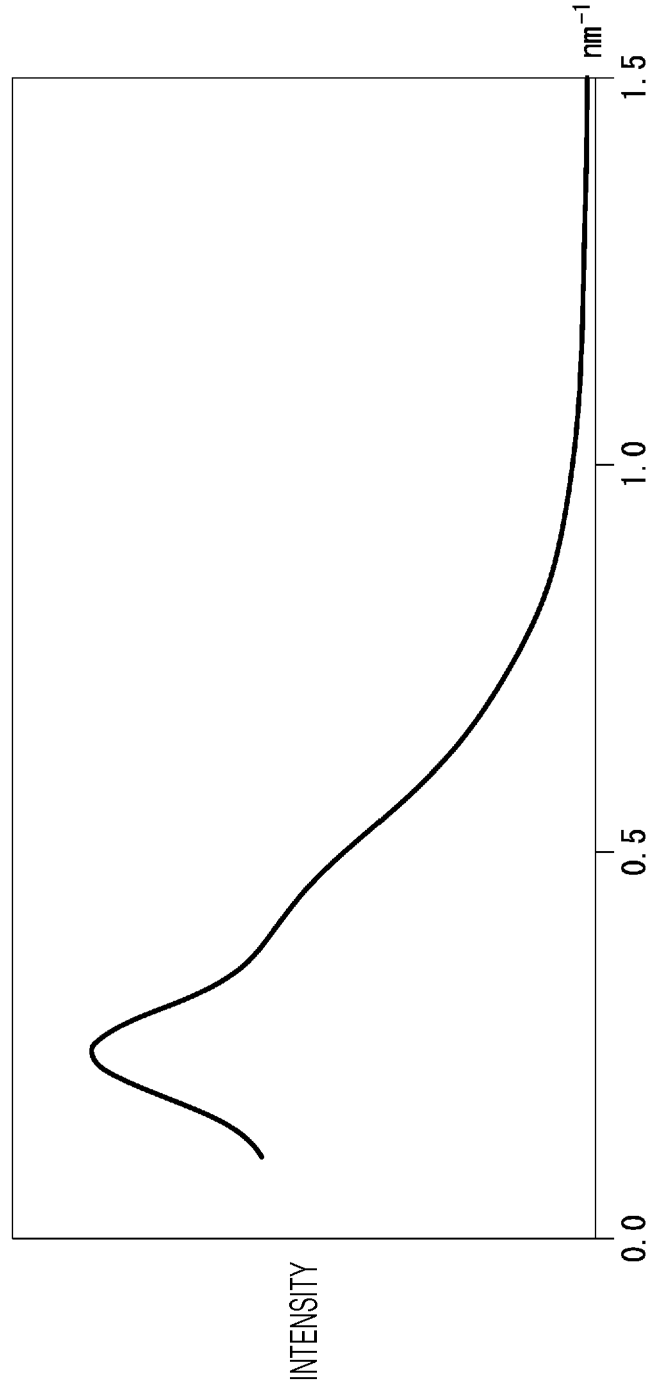
FIG. 7 is a chart illustrating a result of a curve fitting performed on the SAXS scattering curve of Sample A in accordance with embodiments of the present disclosure.

Sample A and Sample B are subjected to small-angle X-ray scattering ("SAXS") in a vacuum atmosphere using a NANOSTAR X-ray scattering system manufactured by Bruker Corporation. CuKα rays are used as X-rays, and the output is set to 45 kV/120 mA. The camera length is 104.4 cm, and the exposure time is 180 minutes. A SAXS scattering curve is illustrated in FIG. 6 where the wavelength is taken along the abscissa and the intensity is taken along the ordinate. Furthermore, the SAXS scattering curve of Sample A is subjected to curve fitting, the result of which is illustrated in FIG. 7.

Figure 8:
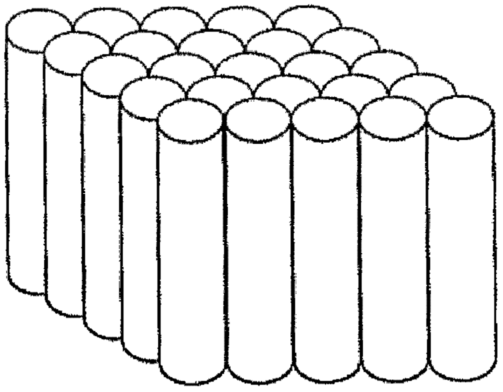
FIG. 8 is a schematic view of an ideal crystal in accordance with embodiments of the present disclosure.
Figure 9:
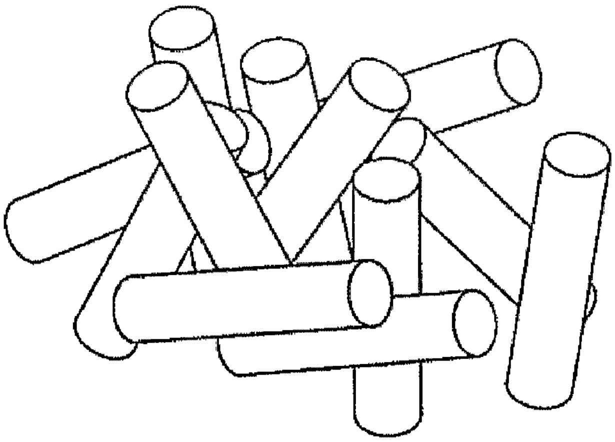
FIG. 9 is a schematic view of amorphousness in accordance with embodiments of the present disclosure.
Figure 10A:
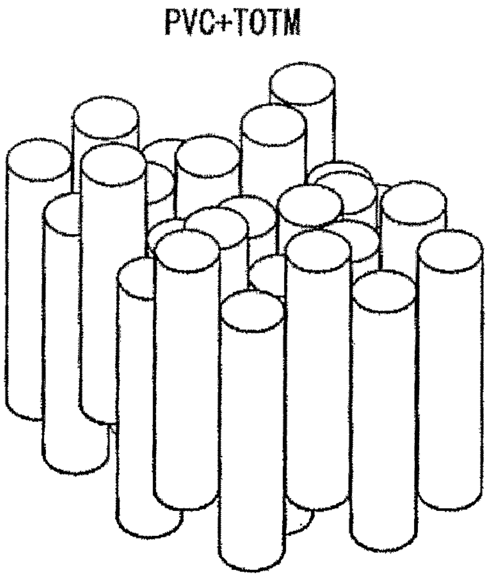
FIGS. 10A and 10B are schematic views of a tissue of Sample A in accordance with embodiments of the present disclosure.

FIG. 8 schematically illustrates an ideal crystal. In the ideal crystal, atoms are arranged regularly. FIG. 9 schematically illustrates amorphousness. The amorphousness has irregularly arranged atoms. As illustrated in FIG. 10A, Sample A has a structure where crystalline regions and an amorphous region are mixed, but it is inferred from FIGS. 6 and 7 that the amorphous region is less disordered and that the crystalline regions and the amorphous region are clearly separated. In other words, as illustrated in FIG. 10B, Sample A has clear boundaries between the crystalline regions and the amorphous region.

Figure 11:
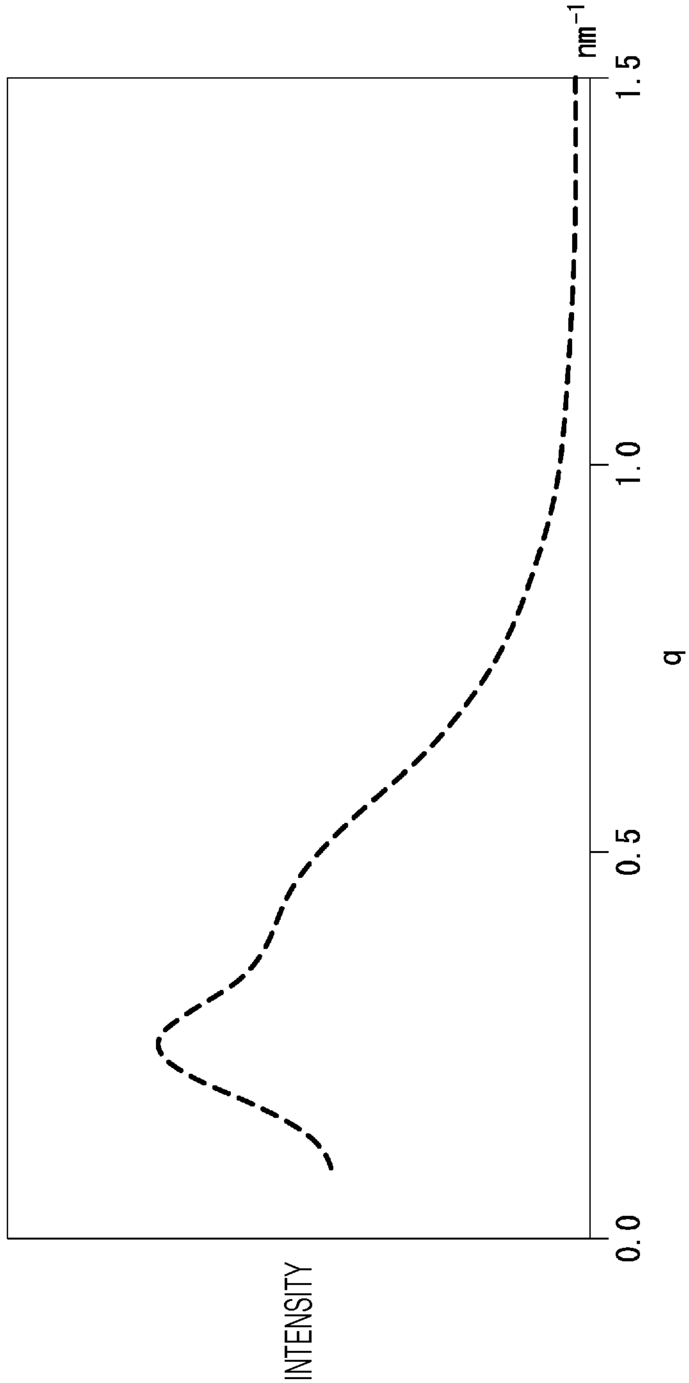
FIG. 11 is a chart illustrating a result of curve fitting performed on the SAXS scattering curve of Sample B in accordance with embodiments of the present disclosure.
Figure 12A:
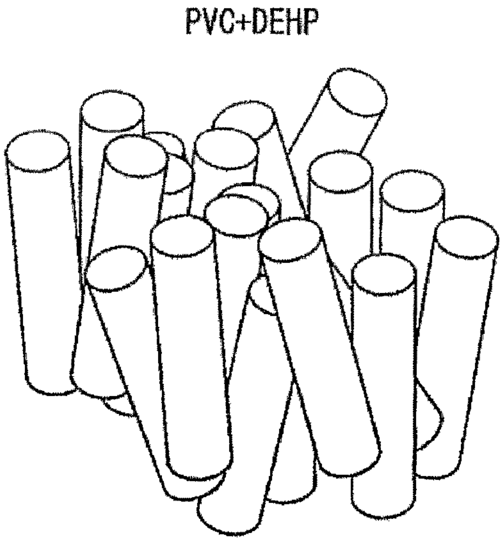
FIGS. 12A and 12B are schematic views of a tissue of Sample B in accordance with embodiments of the present disclosure.
Figure 12B:
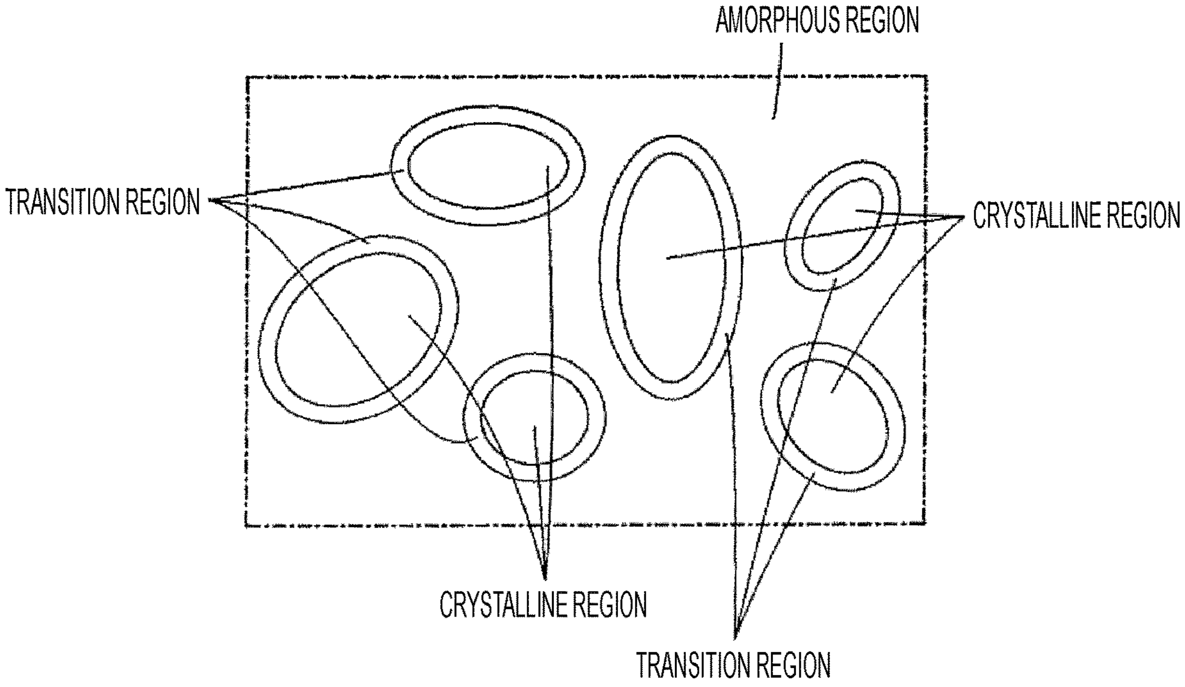

In a similar manner, the SAXS scattering curve of Sample B is also subjected to curve fitting, the result of which is illustrated in FIG. 11. As illustrated in FIG. 12A, Sample B has a structure where the degree of disorder of an amorphous region is larger than that of Sample A, and it is inferred from FIGS. 6 and 11 that crystalline regions and the amorphous region are not clearly separated. In other words, as illustrated in FIG. 12B, between the crystalline regions and the amorphous region, Sample B has transition regions where the crystalline regions and the amorphous region are mixed. Therefore, boundaries between the crystalline regions and the amorphous region are unclear.

Figure 10B:
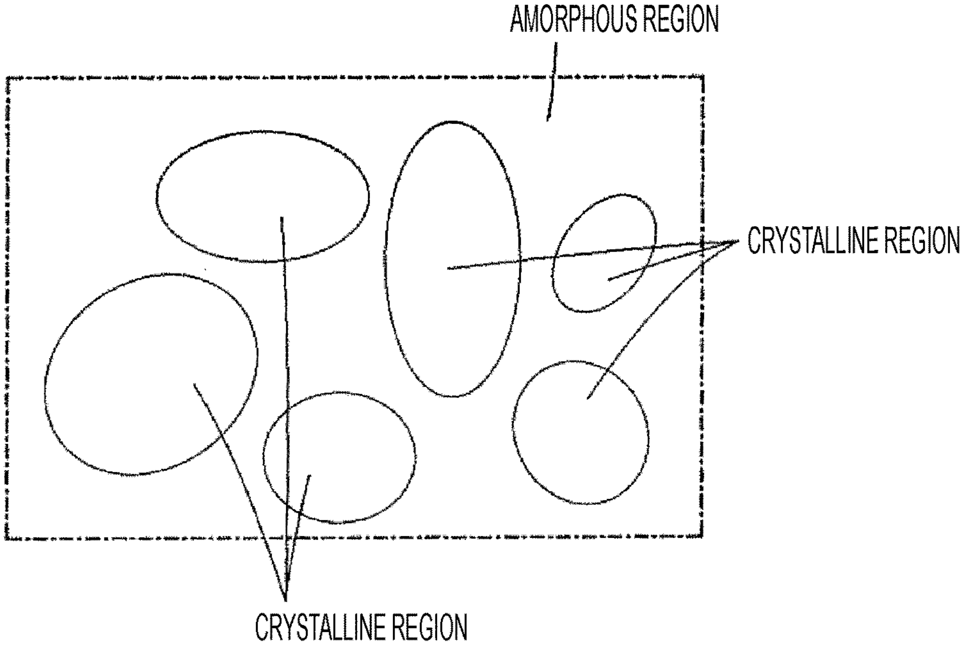

In the structure illustrated in FIG. 10B, stresses are concentrated on interfaces between the crystalline regions and the amorphous region. In contrast, in the structure illustrated in FIG. 12B, it is relatively difficult to cause stress concentration on interfaces between the crystalline regions and the amorphous region. This arrangement is considered to be one reason why the protector 16 is easily separated from the needle hub 14 in the embodiment described above.

EXAMPLE 5

Figure 13:
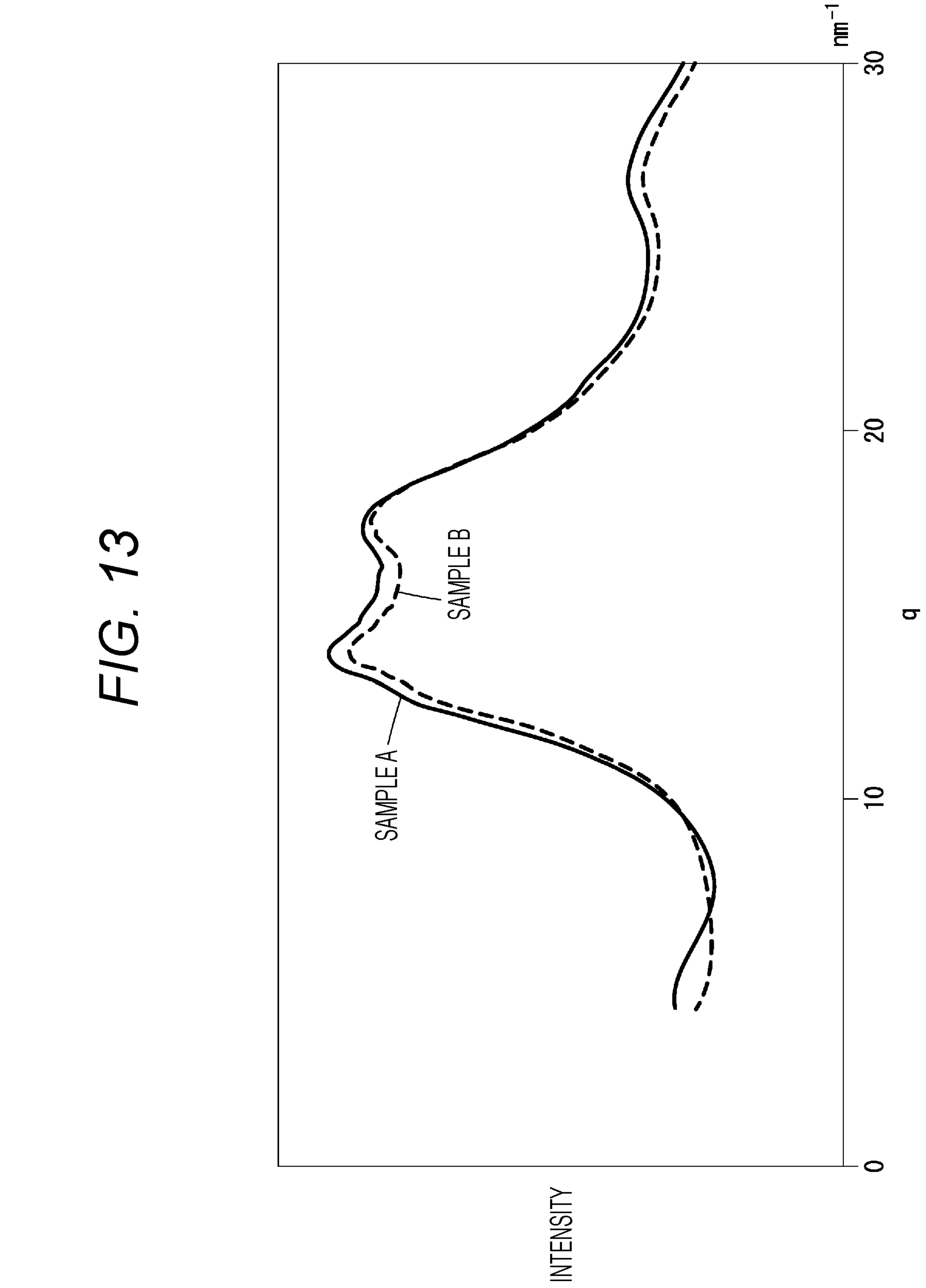
FIG. 13 illustrates wide-angle X-ray scattering ("WAXS") scattering curves obtained by performing WAXS on Sample A and Sample B in accordance with embodiments of the present disclosure.

According to a fifth example, a wide angle X-ray scattering ("WAXS") is performed on each of Sample A and Sample B in a similar manner to the aforementioned fourth example except that the camera length is 4.55 cm and the exposure time is 60 minutes. A WAXS scattering curve is illustrated in FIG. 13 where the wavelength is taken along the abscissa and the intensity is taken along the ordinate.

Figure 14:
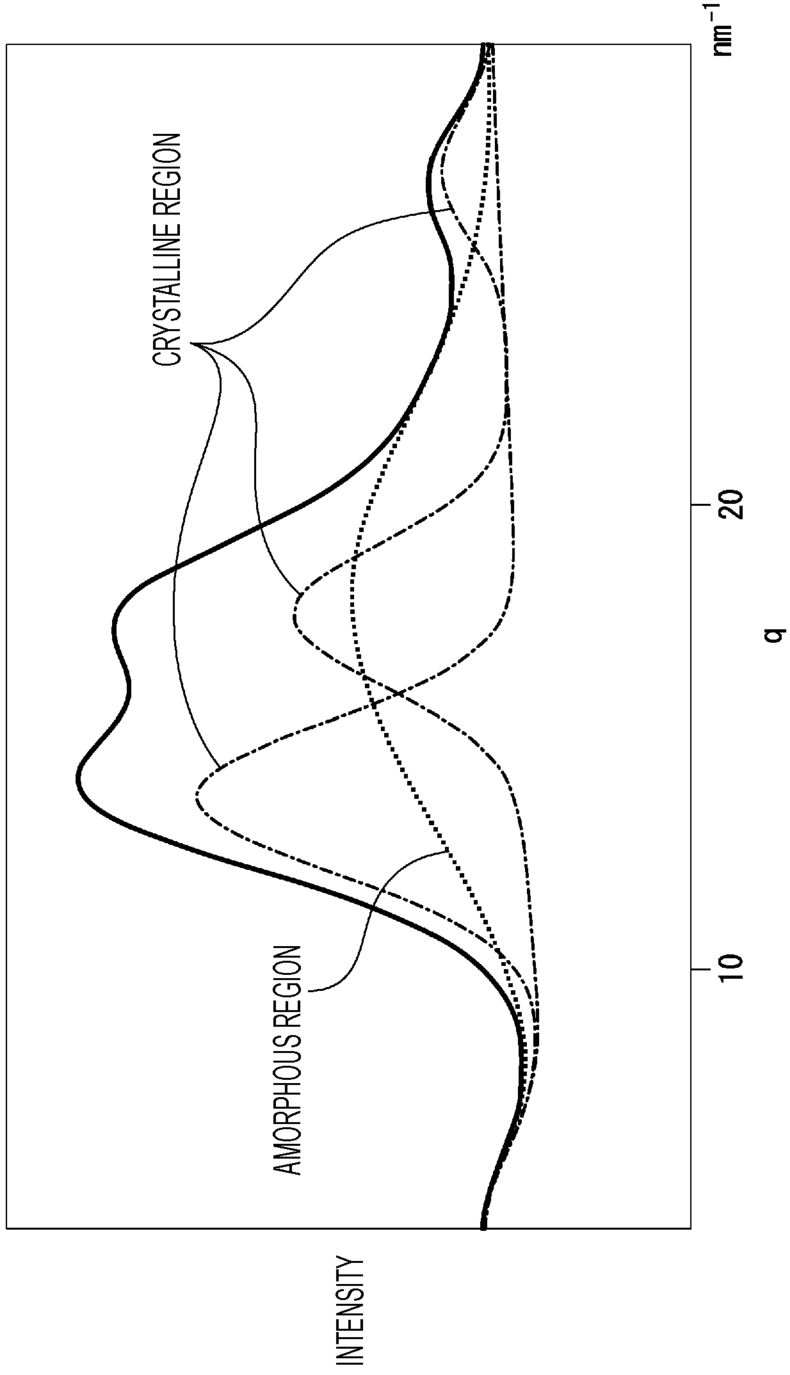
FIG. 14 is a chart illustrating peaks separated for analysis on the WAXS scattering curve of Sample A in accordance with embodiments of the present disclosure.

Peaks in the WAXS scattering curve of Sample A are separated for analysis, the result of which is illustrated in FIG. 14. Dash-dotted lines in FIG. 14 indicate peaks derived from the crystalline regions. A dashed line in FIG. 14 indicates a peak derived from the amorphous region. A crystallinity index is calculated from the following Formula based on a total area of peaks derived from the crystalline regions and an area of a peak derived from the amorphous region.

Formula 1

$$\text{CRYSTALLINITY INDEX [\%]} = \frac{\text{TOTAL AREA OF PEAKS DERIVED FROM CRYSTALLINE REGIONS}}{\text{TOTAL AREA OF PEAKS DERIVED FROM CRYSTALLINE REGIONS} + \text{AREA OF PEAK DERIVED FROM AMORPHOUS REGION}} \times 100$$

The crystallinity index of Sample A calculated using the above Formula is 57%.

Figure 15:
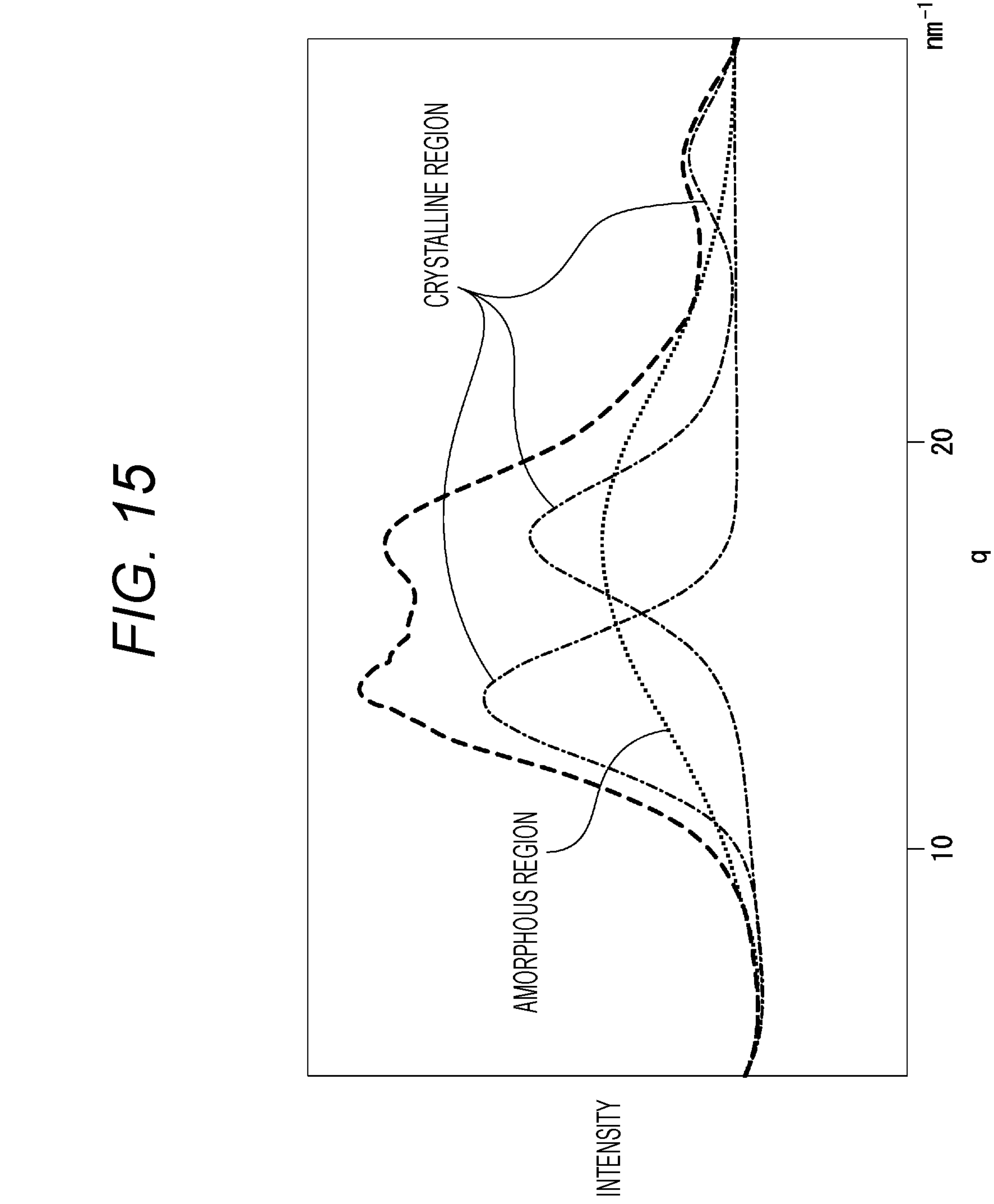
FIG. 15 is a chart illustrating peaks separated for analysis on the WAXS scattering curve of Sample B in accordance with embodiments of the present disclosure.

Peaks in the WAXS scattering curve of Sample B are also separated for analysis, the result of which is illustrated in FIG. 15. Like FIG. 14, the dash-dotted lines indicate peaks derived from the crystalline regions, and a thin dashed line indicates a peak derived from the amorphous region. The crystallinity index of Sample B calculated using the above Formula is 59%.

The crystallinity index of Sample A is smaller than the crystallinity index of Sample B. However, in Sample A, as described above, there are clear interfaces between the crystalline regions and the amorphous region. Based on this result, it is inferred that the blood sampling needle 10 according to this embodiment enables separation of the protector 16 from the needle hub 14 with small rotary torque.

Although the present disclosure has been described above with reference to preferred embodiments, the present disclosure is not limited to the above embodiments, and it goes without saying that various modifications can be made without departing from the gist of the present disclosure.

References in the specification to "one embodiment," "an embodiment," "an example embodiment," "some embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in conjunction with one embodiment, it is submitted that the description of such feature, structure, or characteristic may apply to any other embodiment unless so stated and/or except as will be readily apparent to one skilled in the art from the description. The present disclosure, in various embodiments, configurations, and aspects, includes components, methods, processes, systems and/or apparatus substantially as depicted and described herein, including various embodiments, subcombinations, and subsets thereof. Those of skill in the art will understand how to make and use the systems and methods disclosed herein after understanding the present disclosure. The present disclosure, in various embodiments, configurations, and aspects, includes providing devices and processes in the absence of items not depicted and/or described herein or in various embodiments, configurations, or aspects hereof, including in the absence of such items as may have been used in previous devices or processes, e.g., for improving performance, achieving case, and/or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments, configurations, or aspects for the purpose of streamlining the disclosure. The features of the embodiments, configurations, or aspects of the disclosure may be combined in alternate embodiments, configurations, or aspects other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment, configuration, or aspect. Thus, the following claims are hereby incorporated into this Detailed Description, with each claim standing on its own as a separate preferred embodiment of the disclosure.

Moreover, though the description of the disclosure has included description of one or more embodiments, configurations, or aspects and certain variations and modifications, other variations, combinations, and modifications are within the scope of the disclosure, e.g., as may be within the skill and knowledge of those in the art, after understanding the present disclosure. It is intended to obtain rights, which include alternative embodiments, configurations, or aspects to the extent permitted, including alternate, interchangeable and/or equivalent structures, functions, ranges, or steps to those claimed, whether or not such alternate, interchangeable and/or equivalent structures, functions, ranges, or steps are disclosed herein, and without intending to publicly dedicate any patentable subject matter.

It is to be appreciated that any feature described herein can be claimed in combination with any other feature(s) as described herein, regardless of whether the features come from the same described embodiment.

As used herein, the singular forms "a," "an," and "the" are intended to include the plural forms as well, unless the context clearly indicates otherwise. It will be further understood that the terms "include," "including," "includes," "comprise," "comprises," and/or "comprising," when used in this specification, specify the presence of stated features, integers, steps, operations, elements, and/or components, but do not preclude the presence or addition of one or more other features, integers, steps, operations, elements, components, and/or groups thereof. The term "and/or" includes any and all combinations of one or more of the associated listed items.

The term "a" or "an" entity refers to one or more of that entity. As such, the terms "a" (or "an"), "one or more," and "at least one" can be used interchangeably herein. It is also to be noted that the terms "comprising," "including," and "having" can be used interchangeably.

The phrases "at least one," "one or more," "or," and "and/or" are open-ended expressions that are both conjunctive and disjunctive in operation. For example, each of the expressions "at least one of A, B and C," "at least one of A, B, or C," "one or more of A, B, and C," "one or more of A, B, or C," and "A, B, and/or C" means A alone, B alone, C alone, A and B together, A and C together, B and C together, or A, B, and C together. When each one of A, B, and C in the above expressions refers to an element, such as X, Y, and Z, or a class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and this disclosure.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

What is claimed is:

1. A medical needle comprising:
- a needle body;
- a hub that supports a proximal portion of the needle body in a longitudinal direction; and
- a protector that protects the needle body, wherein,
  - the protector has a needle sheath that covers a portion of the needle body exposed from the hub,
  - the needle sheath is separably joined to the hub,
  - the hub includes a first resin composition and the needle sheath includes a second resin composition,
  - the first resin composition contains polyvinyl chloride and a trimellitate which accounts for 10 to 20 phr, and
  - the second resin composition contains polyvinyl chloride and a trimellitate which accounts for 40 to 50 phr.

2. The medical needle of claim 1, wherein the trimellitate in the first resin composition accounts for 13 to 18 phr, and the trimellitate in the second resin composition accounts for 45 to 47 phr.

3. The medical needle of claim 1, wherein the trimellitate in the first resin composition and the trimellitate in the second resin composition is tris (2-ethylhexyl)trimellitate.

4. The medical needle of claim 1, wherein the protector has an outer sheath that covers the needle sheath.

5. The medical needle of claim 4, wherein a material of the outer sheath is the second resin composition that is same as a material of the needle sheath.

6. A needle assembly, comprising:
- a needle body extending a length along a longitudinal direction from a proximal end portion of the needle body to a distal end portion of the needle body;
- a hub extending from a distal end of the hub to a proximal end of the hub, wherein the proximal end portion of the needle body is disposed in a retaining hole of the hub arranged at the distal end of the hub, wherein the distal end portion of the needle body is exposed from the distal end of the hub, and wherein the hub is made from a first material comprising a first resin composition, the first resin composition comprising a polyvinyl chloride base resin and a trimellitate plasticizer, the trimellitate plasticizer making up 10 phr to 20 phr of the first resin composition; and
- a needle protector that is separably attached to the distal end of the hub, the needle protector comprising:
  - an inner sheath portion arranged in a position surrounding a portion of the needle body that is exposed from the hub, wherein the inner sheath portion is separably joined to the hub, wherein the inner sheath portion is made from a second material comprising a second resin composition, the second resin composition comprising a polyvinyl chloride base resin and a trimellitate plasticizer, the trimellitate plasticizer in the second resin composition making up 40 phr to 50 phr of the second resin composition.

7. The needle assembly of claim 6, wherein a total amount of the trimellitate plasticizer in the first resin composition is 13 phr to 18 phr of the first resin composition, and wherein a total amount of the trimellitate plasticizer in the second resin composition is 45 phr to 47 phr of the second resin composition.

8. The needle assembly of claim 6, wherein the trimellitate plasticizer in the first resin composition and the trimellitate plasticizer in the second resin composition is tris(2-ethylhexyl)trimellitate.

9. The needle assembly of claim 6, wherein the needle protector further comprises:
- an outer sheath portion that is arranged in contact with and covering an outermost surface of the inner sheath portion.

10. The needle assembly of claim 9, wherein the outer sheath portion is made from a third material, and wherein the third material comprises the second resin composition.

11. The needle assembly of claim 9, wherein the outer sheath portion is made from a third material, and wherein the third material comprises a third resin composition comprising a different amount of a trimellitate plasticizer than the trimellitate plasticizer in the second resin composition.

12. The needle assembly of claim 6, wherein the needle protector, when in an attached state with the distal end of the hub, seals a space between the needle body and an inside of the inner sheath portion from a space surrounding an outside of the needle protector.

13. The needle assembly of claim 6, wherein the needle protector is separable from the hub when twisted relative to the hub about an axis extending along the longitudinal direction.

14. The needle assembly of claim 6, wherein the needle body is attached to the hub via an adhesive disposed between the proximal end portion of the needle body and the retaining hole of the hub.

15. The needle assembly of claim 6, wherein the trimellitate plasticizer in the first resin composition and the trimellitate plasticizer in the second resin composition is tributyl trimellitate.

16. A medical needle, comprising:
- a needle body extending a length along a longitudinal direction from a proximal end portion of the needle body to a distal end portion of the needle body;
- a hub extending from a distal end of the hub to a proximal end of the hub, wherein the proximal end portion of the needle body is disposed in a retaining hole of the hub arranged at the distal end of the hub, wherein the distal end portion of the needle body is exposed from the distal end of the hub, and wherein the hub is made from a first material comprising a first resin composition, the first resin composition comprising a polyvinyl chloride base resin and a trimellitate plasticizer, the trimellitate plasticizer making up 10 phr to 20 phr of the first resin composition; and
- a needle protector that is separably attached to the distal end of the hub, the needle protector comprising:

an inner sheath portion arranged in a position surrounding a portion of the needle body that is exposed from the hub, wherein the inner sheath portion is separably joined to the hub, wherein the inner sheath portion is made from a second material comprising a second resin composition, the second resin composition comprising a polyvinyl chloride base resin and a trimellitate plasticizer, the trimellitate plasticizer in the second resin composition making up 40 phr to 50 phr of the second resin composition; and an outer sheath portion that is arranged in contact with and covering an outermost surface of the inner sheath portion.

17. The medical needle of claim 16, wherein a total amount of the trimellitate plasticizer in the first resin composition is 13 phr to 18 phr of the first resin composition, and wherein a total amount of the trimellitate plasticizer in the second resin composition is 45 phr to 47 phr of the second resin composition.

18. The medical needle of claim 17, wherein the trimellitate plasticizer in the first resin composition and the trimellitate plasticizer in the second resin composition is tris (2-ethylhexyl) trimellitate.

19. The medical needle of claim 18, wherein the outer sheath portion is made from a third material, and wherein the third material comprises the second resin composition.

20. The medical needle of claim 18, wherein the outer sheath portion is made from a third material, and wherein the third material comprises a third resin composition comprising a different amount of a trimellitate plasticizer than the trimellitate plasticizer in the second resin composition.

* * * * *